US011850187B2

United States Patent
Arba Mosquera et al.

(10) Patent No.: US 11,850,187 B2
(45) Date of Patent: Dec. 26, 2023

(54) METHOD FOR DETERMINING A CURRENT POSITION OF AN EYE OF A PATIENT BASED ON A PURKINJE IMAGE

(71) Applicant: Schwind eye-tech-solutions GmbH, Kleinostheim (DE)

(72) Inventors: Samuel Arba Mosquera, Aschaffenburg (DE); Thomas Klinner, Glattbach (DE); Mario Shraiki, Stockstadt (DE); Nico Triefenbach, Mainaschaff (DE)

(73) Assignee: SCHWIND EYE-TECH-SOLUTIONS GMBH, Kleinostheim (DE)

( * ) Notice: Subject to any disclaimer, the term of this patent is extended or adjusted under 35 U.S.C. 154(b) by 218 days.

(21) Appl. No.: 17/112,326

(22) Filed: Dec. 4, 2020

(65) Prior Publication Data
US 2021/0169692 A1  Jun. 10, 2021

(30) Foreign Application Priority Data

Dec. 6, 2019  (DE) ...................... 10 2019 133 433.0

(51) Int. Cl.
*A61F 9/008* (2006.01)
*A61F 9/009* (2006.01)

(52) U.S. Cl.
CPC ............ *A61F 9/0084* (2013.01); *A61F 9/009* (2013.01); *A61F 2009/00846* (2013.01); *A61F 2009/00872* (2013.01); *A61F 2009/00897* (2013.01)

(58) Field of Classification Search
CPC ................... A61F 9/0084; A61F 9/009; A61F 2009/00846; A61F 2009/00872;
(Continued)

(56) References Cited

U.S. PATENT DOCUMENTS

2004/0143246 A1* 7/2004 Maeda ................... A61F 9/008
 606/5
2007/0219543 A1* 9/2007 Yee ..................... A61F 9/00836
 606/5
(Continued)

FOREIGN PATENT DOCUMENTS

WO 2014145517 A1 9/2014
WO 2014149625 A1 9/2014

OTHER PUBLICATIONS

First Examination Report dated Sep. 11, 2020 in corresponding German Patent Application No. 10 2019 133 433.0.
(Continued)

*Primary Examiner* — Brian T Gedeon
*Assistant Examiner* — Joshua Andrew Schum-Houck
(74) *Attorney, Agent, or Firm* — MEDLER FERRO WOODHOUSE & MILLS PLLC

(57) ABSTRACT

A method is disclosed for determining a current position of an eye of a patient relative to an optical axis of a laser beam of a treatment apparatus. The method includes presetting a criterion characterizing the eye, determining a first target position of the eye relative to the optical axis, positioning a patient interface in a preset area in front of the optical axis, illuminating the eye during an approaching procedure of the patient interface to the eye, capturing a Purkinje image, which is associated with a cornea of the eye, by means of an optical capturing device during the approaching procedure, comparing the captured Purkinje image to the optical axis and determining the current position of the eye depending thereon, comparing the current position to the target position and with a deviation, outputting a control signal to a control device of the treatment apparatus.

43 Claims, 3 Drawing Sheets

(58) Field of Classification Search
CPC ........ A61F 2009/00897; A61F 9/00827; A61F 9/008; A61F 2009/00885; A61B 3/113; G06T 7/70; G06T 2207/30041
See application file for complete search history.

(56) References Cited

U.S. PATENT DOCUMENTS

| | | | |
|---|---|---|---|
| 2011/0187995 A1* | 8/2011 | Frey | A61F 9/00825 351/208 |
| 2015/0335479 A1 | 11/2015 | Shibata et al. | |
| 2016/0095752 A1* | 4/2016 | Srinivasan | A61F 9/00834 606/6 |

OTHER PUBLICATIONS

Lehrbuch von Dan Z. Reinstein: "The Surgeon's Guide to Smile"; ISBN 9781630912659, Slack Incorporated (Verlag), erschienen im Jahr 2018.

Review Veröffentlichung von S. Mosquera et al.: "Centration axis in refractive surgery"; Eye and Vision (2015) 2:4 (2015).

Communication of an Opposition issued in DE Application No. 10 2019 133 433.0, dated Nov. 2, 2022.

* cited by examiner

METHOD FOR DETERMINING A CURRENT POSITION OF AN EYE OF A PATIENT BASED ON A PURKINJE IMAGE

The invention relates to a method for determining a current position of an eye of a patient relative to an optical axis of a laser beam in a neutral pose of a beam deflection device of a treatment apparatus. Further, the invention relates to a treatment apparatus, to a computer program as well as a to a computer-readable medium.

Opacities and scars within the cornea, which can arise by inflammations, injuries or congenital diseases, impair the sight. In particular in case that these pathological and/or unnaturally altered areas of the cornea are located in the axis of vision of the eye, clear sight is considerably disturbed. Hereto, different laser methods by means of corresponding treatment apparatuses are given from the prior art, which can separate a volume body from the cornea and thus improve the sight for a patient. These laser methods are in particular an invasive intervention such that it is of particular advantage for the patient if the intervention is performed in a time as short as possible and to a particularly efficient extent. Therein, the volume body in particular is to only include the altered area of the cornea. Therefore, based on the prior art, it is particularly important to be able to perform an accurate position determination of the devices of the treatment apparatus, which are used in the intervention.

Therefore, it is the object of the present invention to provide a method and a treatment apparatus, by means of which a current position of a patient interface of the treatment apparatus can be captured in improved manner.

This object is solved by a method, a treatment apparatus, a computer program as well as a computer-readable medium according to the independent claims. Advantageous configurations with convenient developments of the invention are specified in the respective dependent claims, wherein advantageous configurations of the method are to be regarded as advantageous configurations of the treatment apparatus, of the computer program and of the computer-readable medium and vice versa.

An aspect of the invention relates to a method for determining a current position of an eye of a patient relative to an optical axis of a laser beam in a neutral pose of a beam deflection device of a treatment apparatus. Presetting a criterion characterizing the eye depending on patient information of the patient is effected. A target position of the eye relative to the optical axis is determined. A patient interface of the treatment apparatus is positioned in a preset area in front of the optical axis. Illuminating the eye by means of an illumination device of the treatment apparatus is effected during an approaching procedure of the patient interface to the eye. A Purkinje image, which is associated with a cornea of the eye, is captured by means of an optical capturing device of the treatment apparatus during the approaching procedure. Comparing the captured Purkinje image to the optical axis and determining the current position of the eye depending thereon are effected. The current position is determined with the target position, and with a deviation of the current position from the target position, output of a control signal to a control device of the treatment apparatus is effected.

Thereby, it is allowed that a current position of the eye can be compared to a target position of the eye depending on the Purkinje image. Thus, the current position of the eye, in particular during a treatment procedure, can be determined in simple manner yet in reliable manner. Thereby, a treatment of the eye can be more patient-friendly performed since a position of the eye can be reliably determined, and thus the treatment can be reliably realized at a correct location of the eye. In particular based on a captured position of the Purkinje image relative to the optical axis, the current position can be determined.

In particular, the beam deflection device has a neutral pose. For example, the beam deflection device can have two mirrors for deflecting the laser beam. Then, the neutral pose is given with a so-called 0/0 pose of the mirrors to each other. With a rotation of the mirrors, the incident laser beam experiences a deflection and thus can for example be positioned on the cornea. Thus, the beam deflection device has a rotational axis, around which the incident laser beam can be rotated depending on the mirror positions. The optical axis in particular describes the position of the laser beam in the neutral pose of the beam deflection device, which can also be referred to as scanner.

According to an advantageous form of configuration, a pupil center of the eye and/or a cornea apex of the eye are preset as the criterion characterizing the eye. In particular, the characterizing criterion can be determined before the treatment by means of the treatment apparatus. For example, the pupil center and/or a cornea apex of the eye can be determined based on topographic and/or tachymetric and/or morphologic data of the untreated cornea. Thereby, the target position of the eye can be reliably determined.

It is also advantageous if a first order or second order Purkinje reflex is captured as the Purkinje image. In particular, a Purkinje image of the first order Purkinje reflex is captured. Thereby, it is allowed that an automatic eye tracking can for example be performed by means of the treatment apparatus since the first order Purkinje reflex is in particular very well optically perceivable by means of a capturing device. Thus, a manual intervention by a user, for example an optician, is not required to be able to perform a corresponding position correction.

Further, it has proven advantageous if with an ascertained deviation during the approaching procedure, a control signal is generated such that a position correction of the patient interface or of the optical axis is performed. In other words, if the determined current position should deviate from the target position, thus, either the patient interface can be positioned to get from the current position to the target position, or the optical axis can be corrected, for example by a correction of the beam deflection device, thus a reorientation of the optical axis can be performed. Thereby, it is allowed that a treatment of the patient can nevertheless be reliably performed even with an ascertained deviation.

It is also advantageous if after an ascertained deviation below a preset deviation threshold value during the approaching procedure, a control signal is generated such that a docking procedure of the patient interface to the eye is performed. For example, if it should happen that a deviation is ascertained, but it is below a preset threshold value, thus, the approaching procedure can nevertheless be further performed and a docking procedure of the patient interface to the eye can be performed subsequent to the approaching procedure. In particular, a treatment of the eye can then be performed after the docking procedure. Thereby, a treatment duration can be reduced since the approaching procedure in particular does not have to be again performed.

Further, it has proven advantageous if after the docking procedure and with a deviation, a control signal is generated such that a position correction of the pupil relative to the patient interface is performed by means of the patient interface. In other words, if a deviation should be ascertained after the docking procedure, thus, a position correction can nevertheless be further performed in that the pupil is in particular displaced relative to the patient interface. Thereby, it is allowed that the treatment duration can be reduced since a position correction is further possible also after the docking procedure.

In a further advantageous form of configuration, a last image of the optical capturing device before the docking procedure is evaluated after the docking procedure, wherein a captured pupil position is compared to the Purkinje image in the evaluation. In particular, a Purkinje image is no longer present after the docking procedure. Thus, a last frame, in which the Purkinje image is still present, is compared to the next frame, in which the Purkinje image is no longer present. Thereby, the pupil position and also a cornea apex or a cornea apex position can thus in particular be reliably efficiently determined since the contact with the patient interface can first be registered at the cornea apex.

It is further advantageous if a last image of the optical capturing device before the docking procedure and a first image of the optical capturing device after the docking procedure are evaluated after the docking procedure, wherein a captured cornea apex position is compared to the Purkinje image in the evaluation. In particular, the Purkinje image has disappeared after the docking procedure. Thus, the location, at which the patient interface now contacts the eye, is in particular the cornea apex position of the eye. Thereby, the cornea apex position can be reliably determined. In particular, the determined cornea apex position can be compared to the preset cornea apex position, which has for example be determined based on patient information, whereby a position determination of the eye can be performed by means of this evaluation methodology too.

It has further proven advantageous if the eye is sucked onto and fixed to the patient interface by means of a suction device of the patient interface after the docking procedure. In particular, a position correction of the patient interface can be performed during the approaching process. After the docking procedure, the eye is then sucked and fixed based on the suction device such that a position displacement of the eye relative to the patient interface can at least substantially no longer occur. Thereby, it is allowed that a treatment of the eye can be reliably performed.

Further, it has proven advantageous if a current pupil position of the eye is additionally captured by means of the optical capturing device for determining the current position. Thus, the position of the eye can in particular be reliably determined also based on an evaluation of the pupil position and in particular by comparing to the preset pupil position. Thus, the position of the eye can be determined in redundant manner. Thereby, a treatment of the eye of the patient is reliably allowed.

It has further proven advantageous if the eye is illuminated by means of an illumination ring or illumination point or by means of an illumination half ring or by means of illumination sectors of the illumination device for generating the Purkinje image. In particular, it is allowed by the different forms of configuration that the Purkinje image can be reliably captured. In particular, the Purkinje reflex can be reliably generated. By the form of configuration of the illumination ring, the illumination point or illumination half ring or by means of illumination sectors, torsions can for example also be recognized, since relative position variations of the illumination device to the Purkinje image can also be captured besides the illumination. Thereby, it is possible that the Purkinje image can be captured by means of different illumination devices.

In a further advantageous form of configuration, with a deviation above a preset deviation threshold value, the approaching procedure is aborted and an approaching procedure is again performed and/or a docking procedure is aborted and a docking procedure is again performed and/or the patient interface is newly positioned as the control signal. Thereby, it is allowed that the control signal is generated in different manner and treatment of the eye is not performed with a deviation above the preset deviation threshold value such that mistreatments cannot occur.

It is also advantageous if with a deviation above a preset deviation threshold value, a position variation of the eye surgical laser, in particular of the optical axis, is performed. For example, this can be performed by a position correction of the beam deflection device. Thus, it is also allowed that the eye surgical laser is also newly positioned such that a treatment of the eye can still be reliably performed reduced in time even with a deviation.

In a further advantageous form of configuration, the eye is illuminated by means of an illumination device arranged at the patient interface and/or the Purkinje image is captured by means of a capturing device arranged at the patient interface. In other words, the capturing device and the illumination device can be arranged at the patient interface. Thereby, it is allowed that the capturing device and the illumination device can be simultaneously and in particular reliably moved with the patient interface, whereby the Purkinje image can be reliably captured during the treatment.

A further aspect of the invention relates to a treatment apparatus with at least one eye surgical laser for the separation of a volume body with predefined interfaces of a human or animal eye for example by means of photodisruption and with at least one control device for the laser or lasers, which is formed to execute the steps of the method according to the preceding aspect.

Therein, the laser is suitable to emit laser pulses in a wavelength range between 300 nm and 1,400 nm, preferably between 700 nm and 1,200 nm, at a respective pulse duration between 1 fs and 1 ns, preferably between 10 fs and 10 ps, and a repetition frequency of greater than 10 kHz, preferably between 100 kHz and 100 MHz.

In an advantageous form of configuration of the treatment apparatus, the treatment apparatus comprises a storage device for at least temporarily storing at least one control dataset, wherein the control dataset or datasets include(s) control data for positioning and/or focusing individual laser pulses in the cornea, and includes at least one beam deflection device for beam guidance and/or beam shaping and/or beam deflection and/or beam focusing of a laser beam of the laser. Therein, the mentioned control datasets are usually generated based on a measured topography and/or tachymetry and/or morphology of the cornea to be treated and the type of the pathologically and/or unnaturally altered area to be removed within the cornea.

Further features and the advantages thereof can be taken from the descriptions of the first inventive aspect, wherein advantageous configurations of each inventive aspect are to be regarded as advantageous configurations of the respectively other inventive aspect.

A third aspect of the invention relates to a computer program including commands, which cause the treatment apparatus according to the second inventive aspect to execute the method steps according to the first inventive aspect. A fourth aspect of the invention relates to a computer-readable medium, on which the computer program according to the third inventive aspect is stored. Further features and the advantages thereof can be taken from the descriptions of the first and the second inventive aspect, wherein advantageous configurations of each inventive aspect are to be regarded as advantageous configurations of the respectively other inventive aspect.

Further features are apparent from the claims, the figures and the description of figures. The features and feature combinations mentioned above in the description as well as the features and feature combinations mentioned below in the description of figures and/or shown in the figures alone are usable not only in the respectively specified combination, but also in other combinations without departing from the scope of the invention. Thus, implementations are also to be considered as encompassed and disclosed by the invention, which are not explicitly shown in the figures and explained, but arise from and can be generated by separated feature combinations from the explained implementations. Implementations and feature combinations are also to be considered as disclosed, which thus do not comprise all of the features of an originally formulated independent claim. Moreover, implementations and feature combinations are to be considered as disclosed, in particular by the implementations set out above, which extend beyond or deviate from the feature combinations set out in the relations of the claims.

The figures show the following.

In the figures, identical or functionally identical elements are provided with the same reference characters.

Figure 1:
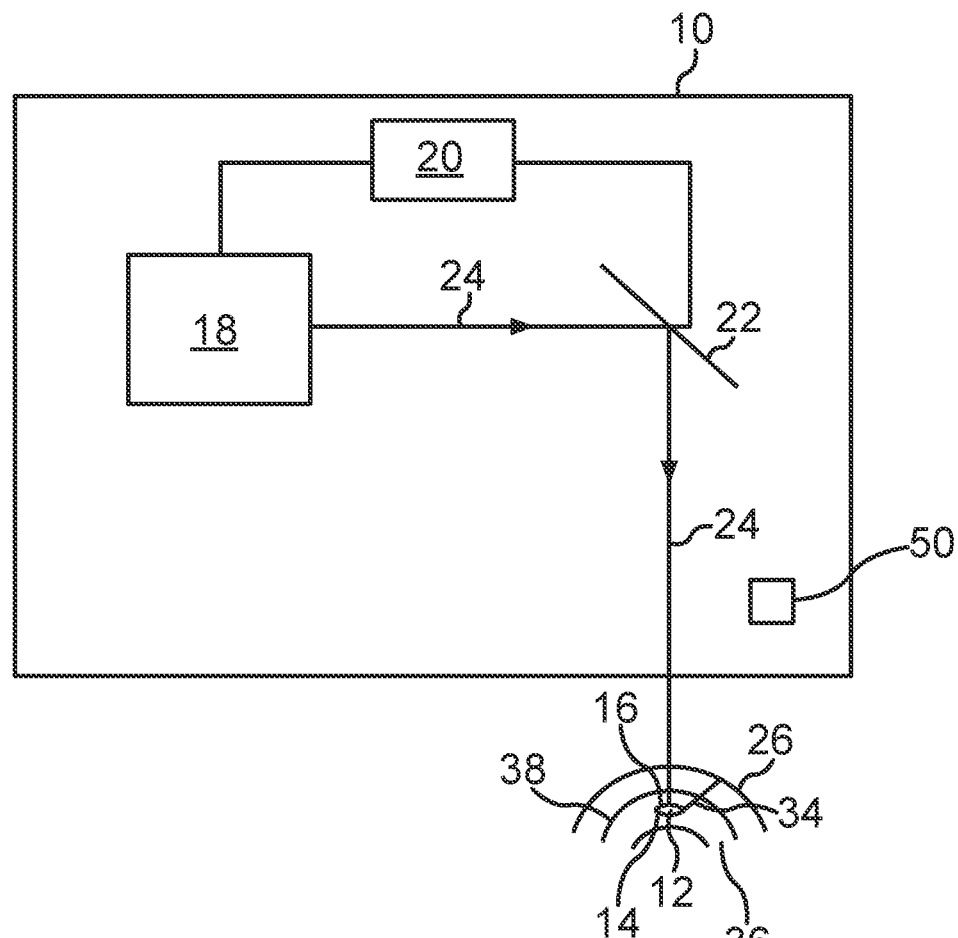
FIG. 1 is a schematic representation of a treatment apparatus according to the invention.

FIG. 1 shows a schematic representation of a treatment apparatus 10 with an eye surgical laser 18 for the separation of a predefined corneal volume or volume body 12 with for example predefined interfaces 14, 16 of a cornea 13 (FIG. 2) of a human or animal eye 3 (FIG. 2) for example by means of photodisruption. One recognizes that a control device 20 for the laser 18 is formed besides the laser 18, such that it emits pulsed laser pulses in a predefined pattern into the cornea 13 in the present embodiment, wherein the interfaces 14, 16 of the volume body 12 to be separated are generated by the predefined pattern by means of photodisruption. In the illustrated embodiment, the interfaces 14, 16 form a lenticular volume body 12, wherein the position of the volume body 12 is selected in this embodiment such that a pathological and/or unnaturally altered area within a stroma 36 of the cornea 13 is enclosed. Furthermore, it is apparent from FIG. 1 that the so-called Bowman's membrane 38 is formed between the stroma 36 and an epithelium 28.

Furthermore, one recognizes that the laser beam 24 generated by the laser 18 is deflected towards a surface 26 of the cornea by means of a beam deflection device 22 such as for example a scanner. The beam deflection device 22 is also controlled by the control device 20 to generate the mentioned predefined pattern in the cornea. The beam deflection device 22 can for example comprise two mirrors, which are formed for deflecting the incident laser beam 24. In a neutral pose, a so-called 0/0 position of the mirrors, an optical axis 4 (FIG. 4) of the laser beam 24 is in particular formed.

The illustrated laser 18 is a photodisruptive laser, which is formed to emit laser pulses in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kHz, preferably between 100 kHz and 100 MHz. Alternatively, to the treatment apparatus 10 shown in FIG. 1, a method for ablative removal of the volume body 12 can also be used.

In addition, the control device 20 comprises a storage device (not illustrated) for at least temporarily storing at least one control dataset, wherein the control dataset or datasets include(s) control data for positioning and/or for focusing individual laser pulses in the cornea 13. The position data and/or focusing data of the individual laser pulses are generated based on a previously measured topography and/or pachymetry and/or the morphology of the cornea and the pathological and/or unnaturally altered area 32 for example to be removed within the stroma 36 of the eye.

Figure 2:
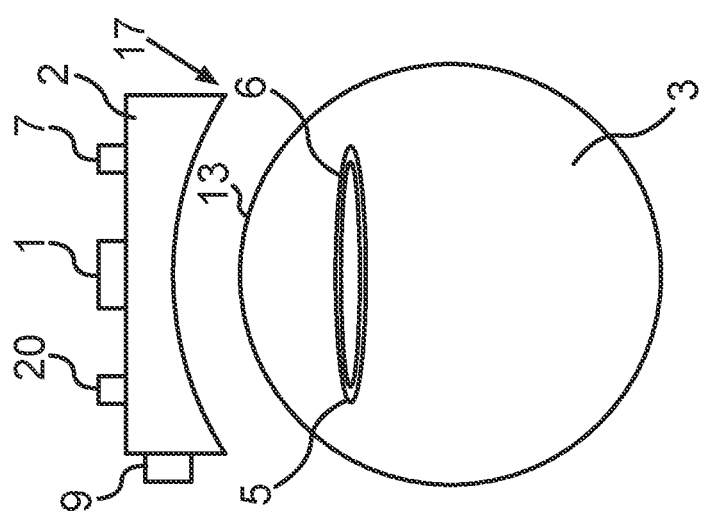
FIG. 2 is a schematic side view of an embodiment of a treatment apparatus with a patient interface in a first situation.

FIG. 2 purely exemplarily shows the treatment apparatus 10 in a schematic side view. The treatment apparatus 10 comprises a patient interface 2. The patient interface 2 is formed for the eye surgical laser 18 of the treatment apparatus 10 for the eye 3 of the patient not illustrated. The patient interface 2 can be coupled to the treatment apparatus 10 for example by means of a connection device 1 for moving the patient interface 2.

In FIG. 2, it is shown that the patient interface 2 can for example have a distance to the eye 3 of for example 5 cm in the illustrated situation. Further, an iris 5 as well as a pupil 6 is shown at the eye 3 in FIG. 2.

In particular, a current pupil position 17 of the eye 3 can be additionally captured by means of the optical capturing device 9 for determining the current position.

Figure 3:
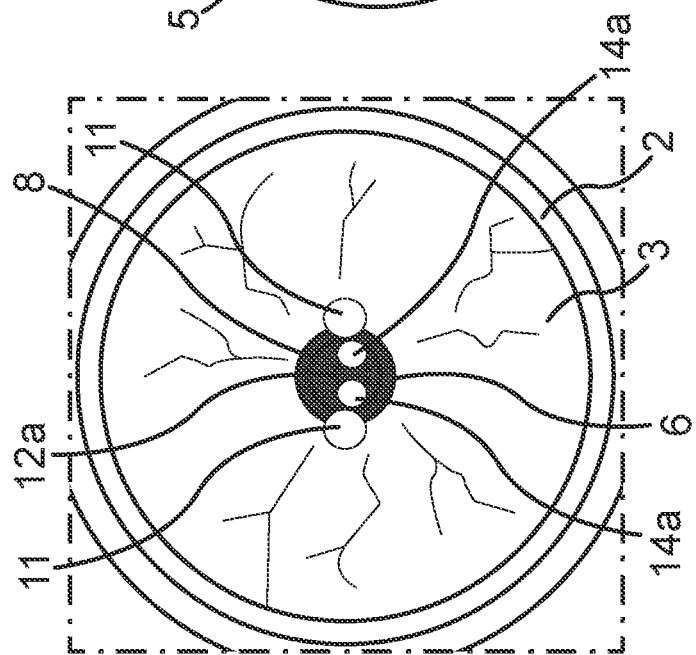
FIG. 3 is a schematic top view to an eye of a patient.

FIG. 3 shows a view through the patient interface 2 to the eye 3 of the patient in a top view. Presently, the pupil 6 is shown hatched.

A method for determining a current position of the eye 3 of the patient relative to an optical axis 4 of the laser beam 24 of the treatment apparatus 10 is shown. A criterion characterizing the eye 3 is preset depending on patient information of the patient. Determining a first target position of the eye 3 relative to the optical axis 4 is effected. The patient interface 2 of the treatment apparatus 10 is positioned in a preset area in front of the optical axis 4. The eye 3 is illuminated by means of an illumination device 7 of the treatment apparatus 10 during an approaching procedure 18a of the patient interface 2 to the eye 3. A Purkinje image 12a, which is associated with a cornea 13 of the eye 3, is captured by means of an optical capturing device 9 of the treatment apparatus 10 during the approaching procedure 18a. The captured Purkinje image 12a is compared to the optical axis 4 and the current position of the eye 3 is determined depending thereon. Comparing the current position to the target position is effected and with a deviation of the current position from the target position, an output of a control signal to the control device 20 of the treatment apparatus 10 is performed.

For example, a pupil center of the eye 3 and/or a cornea apex 15 (FIG. 4) of the eye 3 can be preset as the criterion characterizing the eye 3.

In particular, FIG. 3 further shows that a static projection 11, in particular two static projections 11, are generated by the treatment apparatus 10, in particular by the illumination device 7, on the anterior surface of the patient interface 2. Further, a static projection 8 is shown as a ring on the pupil 6, which is a static projection of the illumination device 7 on the anterior surface of the patient interface 2. The static projection 8 can in particular be a Purkinje image, which is associated with the patient interface 2. Further, a dynamic projection ring is shown, which is generated on an anterior surface of the cornea 13 of the eye 3 and corresponds to the Purkinje image 12a. Further, two dynamic projections 14a of the illumination device 7 are shown, which are generated on the anterior surface of the cornea 13.

In particular, it can be provided that a first order or second order Purkinje reflex is captured as the Purkinje image 12a. Presently, a first order Purkinje reflex is in particular shown.

Further, with an ascertained deviation during the approaching procedure 18a, a control signal can be generated such that a position correction of the patient interface 2 or of the optical axis 4 is performed. Furthermore, it can be provided that after an ascertained deviation below a preset deviation threshold value during the approaching procedure 18a, a control signal is generated such that a docking procedure of the patient interface 2 to the eye 3 is performed. Further, after the docking procedure and with a deviation, a control signal can be generated such that a position correction of the pupil 6 relative to the patient interface 2 is performed by means of the patient interface 2.

The eye 3 can also be illuminated by means of an illumination ring or illumination point or by means of an illumination half ring or by means of illumination sectors as the illumination device 7 for generating the Purkinje image 12a. Similarly, it can be provided that the eye 3 is illuminated with infrared light by means of an infrared illumination device as the illumination device 7 and the optical capturing device 9 is configured such that infrared light reflected on the eye 3 at least in certain areas is captured.

Figure 4:
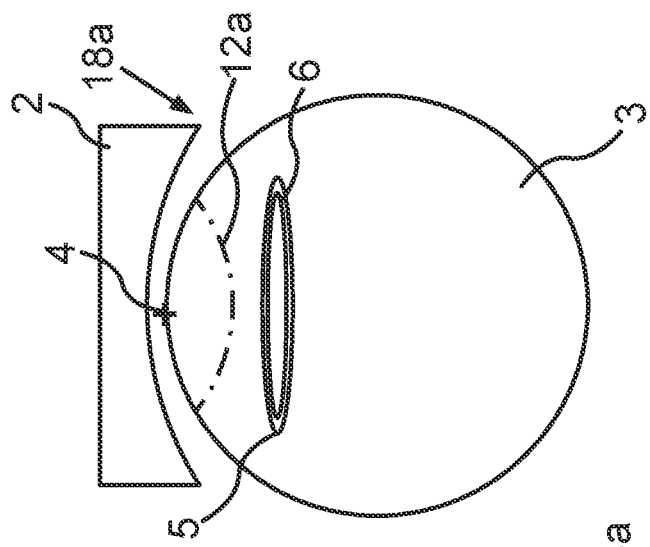
FIG. 4 is a further schematic side view to an embodiment of the patient interface in a further situation.

FIG. 4 shows the patient interface 2 in an approached state in a schematic side view, thus during an approaching procedure 18a to the eye 3. For example, as presently, a distance of the patient interface 2 to the eye 3 can be 2 to 3 mm. In particular, a Purkinje image 12a is shown on the eye 3. In particular, FIG. 4 shows the optical axis 4. For example, if a deviation above a preset deviation threshold value should now be ascertained, thus, the patient interface 2 can be newly positioned. Further, it can be provided that with a deviation above a preset deviation threshold value, a position variation of the eye surgical laser 18, in particular of the optical axis 4, is performed.

Figure 5:
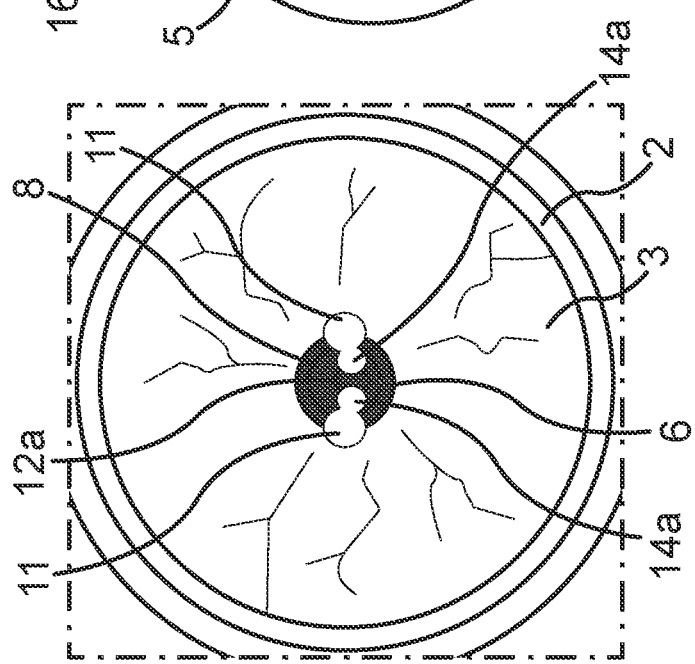
FIG. 5 is a further schematic top view to an eye of a patient.

FIG. 5 shows the eye 3 in a further top view. In FIG. 5, the position of the patient interface 2 is in particular as it is illustrated in the side view in FIG. 4. In FIG. 5, a corresponding displacement and thus a deviation of the current position from the target position can in particular be registered. Based on this displacement, the control signal for the treatment apparatus 10, in particular for controlling the patient interface 2, can now be generated.

Figure 6:
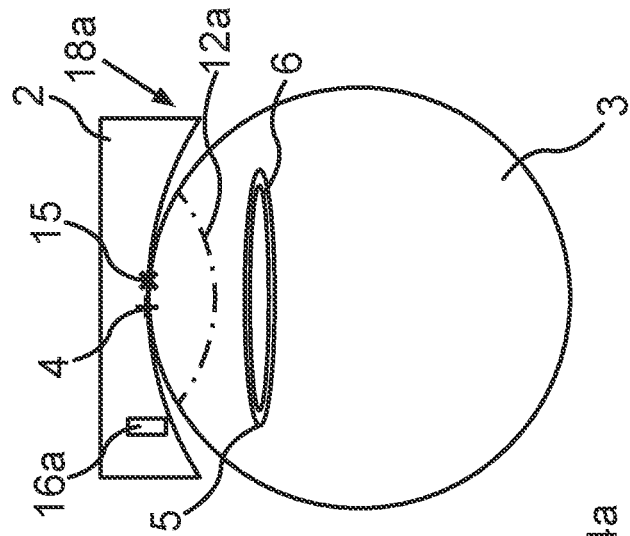
FIG. 6 is a further schematic side view to an embodiment of the patient interface in a further situation.

FIG. 6 shows the eye 3 in a schematic side view during the docking procedure of the patient interface 2. In particular, the patient interface 2 docks to a cornea apex 15 of the eye 3. In particular, the cornea apex 15 is displaced to the optical axis 4. In FIG. 6, it is in particular shown that the patient interface 2 is configured electrically insulated and/or sterile such that electrical voltages cannot transition from the patient interface 2 to the eye 3. In particular, germs either cannot be transferred from the patient interface 2 to the eye 3.

Further, FIG. 6 shows that the eye 3 is sucked onto and fixed to the patient interface 2 by means of a suction device 16a of the patient interface 2 after the docking procedure.

Figure 7:
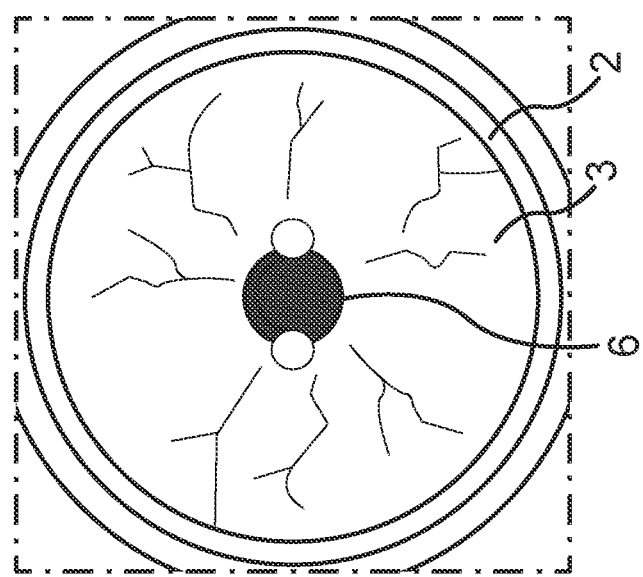
FIG. 7 is a further schematic top view to an eye of a patient in a further situation.

FIG. 7 shows the eye 3 with the patient interface 2 in the top view according to the side view of FIG. 6 in a schematic top view, wherein the Purkinje image 12a herein has nearly disappeared. After the docking procedure, a last image of the optical capturing device 9 before the docking procedure can be evaluated, wherein the captured pupil position 17 can be compared to the Purkinje image 12a in the evaluation. Further, a last image of the optical capturing device 9 before the docking procedure and a first image of the optical capturing device 9 after the docking procedure can be evaluated after the docking procedure, wherein a captured cornea apex position 15 is compared to the Purkinje image 12a in the evaluation.

What is claimed is:

1. A method for determining a current position of an eye of a patient relative to an optical axis of a laser beam formed in a neutral pose of a beam deflection device of a treatment apparatus, comprising the steps of:
   presetting a criterion characterizing the eye depending on patient information of the patient;
   determining a first target position of the eye relative to the optical axis;
   positioning a patient interface of the treatment apparatus in a preset area in front of the optical axis, wherein the patient interface is configured for docking to the eye;
   illuminating the eye with an illumination device of the treatment apparatus during an approaching procedure of the patient interface to the eye;
   capturing a Purkinje image, which is associated with a cornea of the eye, with an optical capturing device of the treatment apparatus during the approaching procedure;
   comparing the Purkinje image to the optical axis and determining the current position of the eye based thereon;
   comparing the current position of the eye to the first target position of the eye, and with a deviation of the current position from the first target position, outputting a control signal to a control device of the treatment apparatus; and
   performing a docking procedure for docking the patient interface to the eye.

2. The method according to claim 1, wherein a pupil center of the eye and/or a cornea apex of the eye are preset as the criterion characterizing the eye.

3. The method according to claim 1, wherein a first order or a second order Purkinje reflex is captured as the Purkinje image.

4. The method according to claim 1, wherein with an ascertained deviation during the approaching procedure, the control signal is generated such that a position correction of the patient interface or of the optical axis is performed.

5. The method according to claim 1, wherein when an ascertained deviation is below a preset deviation threshold value during the approaching procedure, the control signal is generated such that the docking procedure of the patient interface to the eye is performed.

6. The method according to claim 5, wherein after the docking procedure and with the ascertained deviation, a control signal is generated such that a position correction of a pupil relative to the patient interface is performed by the patient interface.

7. The method according to claim 1, further comprising, after performing the docking procedure, evaluating a last image of the optical capturing device taken before the docking procedure, wherein a captured pupil position is compared to the Purkinje image in the evaluation.

8. The method according to claim 1, further comprising, after performing the docking procedure, evaluating a last image of the optical capturing device taken before the docking procedure and a first image of the optical capturing device taken after the docking procedure, wherein a captured cornea apex position is compared to the Purkinje image in the evaluation.

9. The method according to claim 1, wherein the eye is sucked onto and fixed to the patient interface by a suction device of the patient interface after performing the docking procedure.

10. The method according to claim 1, wherein a current pupil position of the eye is additionally captured by the optical capturing device for determining the current position.

11. The method according to claim 1, wherein the eye is illuminated by an illumination ring or an illumination point or by an illumination half ring or by illumination sectors of the illumination device for generating the Purkinje image.

12. The method according to claim 1, wherein with the deviation above a preset deviation threshold value, the approaching procedure is aborted and a further approaching procedure is performed, and/or the docking procedure is aborted and a further docking procedure is performed, and/or the patient interface is newly positioned and the control signal is generated.

13. The method according to claim 1, wherein with the deviation above a preset deviation threshold value, a position variation of the laser beam, in particular of the optical axis, is performed.

14. The method according to claim 1, wherein the eye is illuminated by the illumination device arranged at the patient interface and/or the Purkinje image is captured by the optical capturing device arranged at the patient interface.

15. A treatment apparatus comprising:
at least one surgical laser for separation of a volume body of a human or animal eye of a patient;
at least one control device for the at least one surgical laser; and
a patient interface for docking to the human or animal eye, the treatment apparatus being configured to execute the following method steps:
presetting a criterion characterizing the human or animal eye depending on patient information of the patient;
determining a first target position of the human or animal eye relative to an optical axis;
positioning the patient interface of the treatment apparatus in a preset area in front of the optical axis;
illuminating the eye with an illumination device of the treatment apparatus during an approaching procedure of the patient interface to the human or animal eye;
capturing a Purkinje image, which is associated with a cornea of the human or animal eye, by an optical capturing device of the treatment apparatus during the approaching procedure;
comparing the Purkinje image to the optical axis and determining a current position of the human or animal eye based thereon; and
comparing the current position of the human or animal eye to the first target position of the human or animal eye and with a deviation of the current position from the target position, outputting a control signal to a control device of the treatment apparatus.

16. The treatment apparatus according to claim 15, wherein a pupil center of the human or animal eye and/or a cornea apex of the human or animal eye are preset as the criterion characterizing the human or animal eye.

17. The treatment apparatus according to claim 15, wherein a first order or a second order Purkinje reflex is captured as the Purkinje image.

18. The treatment apparatus according to claim 15, wherein with an ascertained deviation during the approaching procedure, a control signal is generated such that a position correction of the patient interface or of the optical axis is performed.

19. The treatment apparatus according to claim 15, wherein when an ascertained deviation is below a preset deviation threshold value during the approaching procedure, a control signal is generated such that a docking procedure of the patient interface to the human or animal eye is performed.

20. The treatment apparatus according to claim 19, wherein after the docking procedure and with the ascertained deviation, the control signal is generated such that a position correction of a pupil relative to the patient interface is performed by means of the patient interface.

21. The treatment apparatus according to claim 19, wherein after the docking procedure, a last image of the optical capturing device taken before the docking procedure is evaluated, wherein a captured pupil position is compared to the Purkinje image in the evaluation.

22. The treatment apparatus according to claim 19, wherein after the docking procedure, a last image of the optical capturing device taken before the docking procedure and a first image of the optical capturing device taken after the docking procedure are evaluated, wherein a captured cornea apex position is compared to the Purkinje image in the evaluation.

23. The treatment apparatus according to claim 19, wherein after the docking procedure, the human or animal eye is sucked onto and fixed to the patient interface by a suction device of the patient interface.

24. The treatment apparatus according to claim 15, wherein a current pupil position of the human or animal eye is additionally captured by means of the optical capturing device for determining the current position.

25. The treatment apparatus according to claim 15, wherein the human or animal eye is illuminated by an illumination ring or illumination point or by an illumination half ring or by illumination sectors of the illumination device for generating the Purkinje image.

26. The treatment apparatus according to claim 15, wherein with the deviation above a preset deviation threshold value, the approaching procedure is aborted and a further approaching procedure is performed, and/or a docking procedure is aborted and a further docking procedure is performed, and/or the patient interface is newly positioned and the control signal is generated.

27. The treatment apparatus according to claim 15, wherein with the deviation above a preset deviation threshold value, a position variation of the eye surgical laser, in particular of the optical axis, is performed.

28. The treatment apparatus according to claim 15, wherein the human or animal eye is illuminated by the illumination device arranged at the patient interface and/or the Purkinje image is captured by the optical capturing device arranged at the patient interface.

29. The treatment apparatus according to claim 15, wherein the control device comprises at least one storage device for at least temporarily storing at least one control dataset, wherein the at least one control dataset include(s) control data for positioning and/or for focusing individual laser pulses in the cornea, and wherein the at least one control dataset include(s) control data for positioning the patient interface, and includes at least one beam deflection device for beam guidance and/or beam shaping and/or beam deflection and/or beam focusing of a laser beam of the at least one surgical laser.

30. A non-transitory computer-readable medium having instructions stored thereon that, when executed by a processor, cause the processor to determine a current position of an eye of a patient relative to an optical axis of a laser beam formed in a neutral pose of a beam deflection device of a treatment apparatus, the processor:
 presetting a criterion characterizing the eye depending on patient information of the patient;
 determining a first target position of the eye relative to the optical axis;
 positioning a patient interface of the treatment apparatus in a preset area in front of the optical axis, wherein the patient interface is configured for docking to the eye;
 illuminating the eye with an illumination device of the treatment apparatus during an approaching procedure of the patient interface to the eye;
 capturing a Purkinje image, which is associated with a cornea of the eye, with an optical capturing device of the treatment apparatus during the approaching procedure;
 comparing the captured Purkinje image to the optical axis and determining the current position of the eye based thereon;
 comparing the current position of the eye to the first target position of the eye and with a deviation of the current position from the first target position, outputting a control signal to a control device of the treatment apparatus; and
 performing a docking procedure for docking the patient interface to the eye.

31. The non-transitory computer-readable medium of claim 30, wherein a pupil center of the eye and/or a cornea apex of the eye are preset as the criterion characterizing the eye.

32. The non-transitory computer-readable medium of claim 30, wherein a first order or a second order Purkinje reflex is captured as the Purkinje image.

33. The non-transitory computer-readable medium of claim 30, wherein with an ascertained deviation during the approaching procedure, the control signal is generated such that a position correction of the patient interface or of the optical axis is performed.

34. The non-transitory computer-readable medium of claim 30, wherein when an ascertained deviation is below a preset deviation threshold value during the approaching procedure, the control signal is generated such that the docking procedure of the patient interface to the eye is performed.

35. The non-transitory computer-readable medium of claim 34, wherein after the docking procedure and with the ascertained deviation, the control signal is generated such that a position correction of a pupil relative to the patient interface is performed by the patient interface.

36. The non-transitory computer-readable medium of claim 30, wherein after the docking procedure, a last image of the optical capturing device taken before the docking procedure is evaluated, wherein a captured pupil position is compared to the Purkinje image in the evaluation.

37. The non-transitory computer-readable medium of claim 30, wherein after the docking procedure a last image of the optical capturing device taken before the docking procedure and a first image of the optical capturing device taken after the docking procedure are evaluated, wherein a captured cornea apex position is compared to the Purkinje image in the evaluation.

38. The non-transitory computer-readable medium of claim 34, wherein the eye is sucked onto and fixed to the patient interface by a suction device of the patient interface after the docking procedure.

39. The non-transitory computer-readable medium of claim 30, wherein a current pupil position of the eye is additionally captured by the optical capturing device for determining the current position.

40. The non-transitory computer-readable medium of claim 30, wherein the eye is illuminated by an illumination ring or an illumination point or by an illumination half ring or by illumination sectors of the illumination device for generating the Purkinje image.

41. The non-transitory computer-readable medium of claim 30, wherein with the deviation above a preset deviation threshold value, the approaching procedure is aborted and a further approaching procedure is performed, and/or the docking procedure is aborted and a further docking procedure is performed, and/or the patient interface is newly positioned and the control signal is generated.

42. The non-transitory computer-readable medium of claim 30, wherein with the deviation above a preset deviation threshold value, a position variation of the laser beam, in particular of the optical axis, is performed.

43. The non-transitory computer-readable medium of claim 30, wherein the eye is illuminated by the illumination device arranged at the patient interface and/or the Purkinje image is captured by the optical capturing device arranged at the patient interface.

* * * * *